United States Patent [19]

Kellie

[11] Patent Number: 4,520,388
[45] Date of Patent: May 28, 1985

[54] OPTICAL SIGNAL PROJECTOR

[75] Inventor: Truman F. Kellie, West Chester, Ohio

[73] Assignee: General Electric Company, Cincinnati, Ohio

[21] Appl. No.: 438,141

[22] Filed: Nov. 1, 1982

[51] Int. Cl.³ .................... G01B 11/00; H04N 7/18
[52] U.S. Cl. ............................ 358/107; 358/106; 356/376
[58] Field of Search .............. 358/294, 93, 106, 107; 356/376, 1; 250/237 G

[56] References Cited

U.S. PATENT DOCUMENTS

| 3,619,065 | 11/1971 | Agnew | 356/376 |
| 3,794,427 | 2/1974 | Shibata et al. | 356/120 |
| 3,814,521 | 6/1974 | Free | 356/156 |
| 4,175,862 | 11/1979 | DiMatteo et al. | 356/375 |
| 4,349,277 | 9/1982 | Mundy et al. | 356/376 |
| 4,427,880 | 1/1984 | Kanade et al. | 356/376 |

OTHER PUBLICATIONS

U.S. application Ser. No. 158,372, filed 6/11/80—Mundy et al., Allowed 5/14/82.

Primary Examiner—Howard W. Britton
Assistant Examiner—Victor R. Kostak
Attorney, Agent, or Firm—Gregory A. Welte; Derek P. Lawrence

[57] ABSTRACT

An invention is disclosed in which a light source provides light beams of different wavelengths which are projected to an object to form images thereon at substantially the same degree of focus and magnification. The reflected images are received by two photosensors, each responsive to one of the wavelengths, which produce signals indicative of surface features of the object. Increased resolution of small surface features is obtained through the similarities of focus and magnification.

22 Claims, 5 Drawing Figures

OPTICAL SIGNAL PROJECTOR

The invention relates to optical illumination systems and, more particularly, to such systems which illuminate a surface to be inspected by projecting an image thereon.

BACKGROUND OF THE INVENTION

Radiation of different wavelengths, such as visible and infrared radiation, is focused at different focal points by a given lens. For example, radiation of relatively short wavelength, such as visible light, will focus at a point nearer to a lens than radiation of relatively long wavelength, such as infrared radiation. Further, the size of the image focused at the focal point is a function of the distance from the focal point to the lens. Thus, in an optical system where the object is illuminated by radiation of different wavelengths, the visible image and the infrared image, if both are in focus, will be noncoincident in space and of different magnifications.

Some optical inspection systems may project images by using radiation of different wavelengths and may transmit the images along a common path through common lenses. In such a case, a limit is imposed upon the degree of precision or resolution of the system by the noncoincidence of the focused images and by the different magnifications of the focused images resulting from the different wavelengths used.

OBJECTS OF THE INVENTION

It is an object of the present invention to provide a new and improved optical image projector.

It is a further object of the present invention to provide a new and improved optical projector for projecting two images of an object illuminated with radiation of different wavelengths such that the images will be spatially coincident with identical magnification and both will be substantially in focus.

SUMMARY OF THE INVENTION

One form of the present invention extracts light of two different wavelengths from a common source beam and projects the beams to an object to be examined at substantially the same degree of focus and substantially the same magnification.

DETAILED DESCRIPTION OF THE INVENTION

Figure 1:
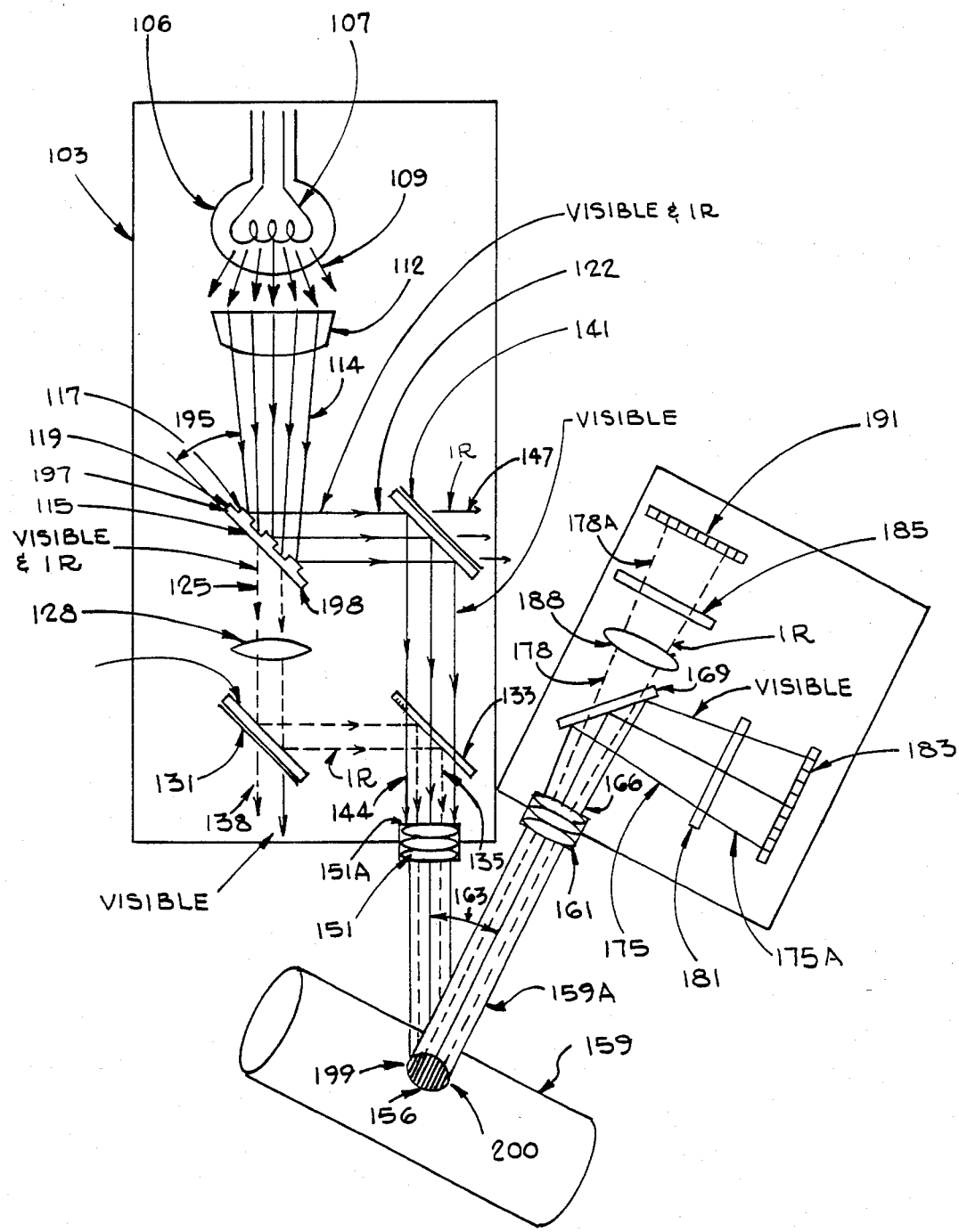
FIG. 1 is a schematic view of one form of the present invention.

In FIG. 1, an optical projector 103 contains a source of illumination 106, such as a 24 volt tungsten filament light bulb, which source 106 emits light indicated as rays 109. The filament 107 of the source 106 is viewed as providing a line-source of light. A condensing lens 112, such as Model No. 60359, available from Edmund Scientific Co., Barrington, N.J., placed so as to cast an image of the source 106 at the entrance pupil 151A of a lens 151, captures many of rays 109 and focuses them as an incoming light beam 114 in the direction of a reflective grating such as patterned mirror 115. The condensing lens 112 is preferably a short focal length, single element lens of approximately 1 to 2 inches (2.54 to 5.08 cm) in diameter.

Figure 2:
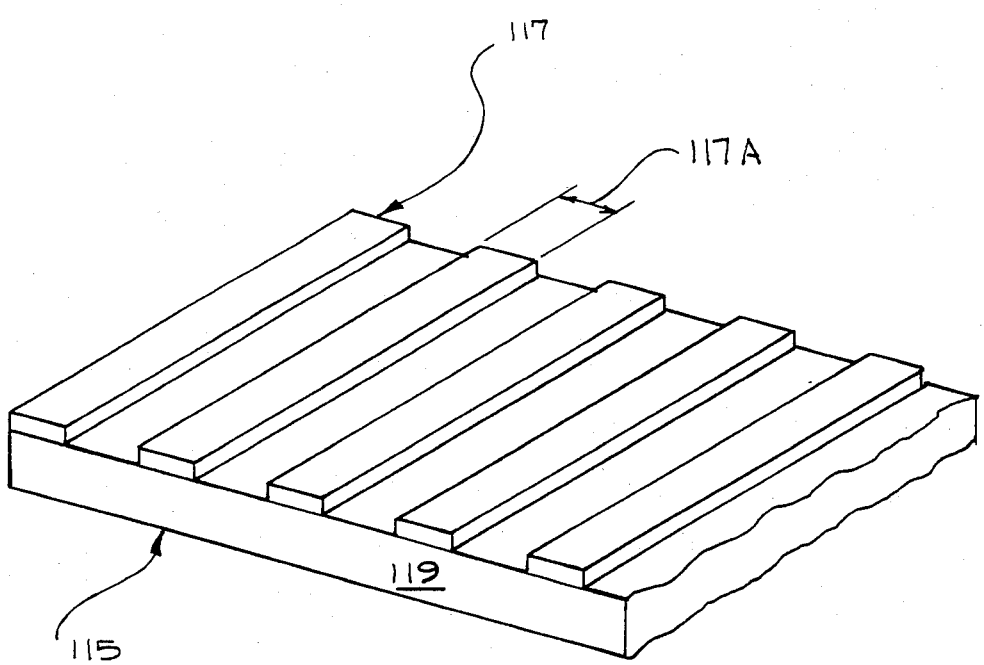
FIG. 2 is a view of one kind of reflective grating of the present invention.

The patterned mirror 115, as shown in FIG. 2, preferably bears a pattern of alternating reflective metal strips 117 deposited on the surface of a sheet of glass 119. The strips 117 are preferably of equal width (dimension 117A) and equally spaced at a spatial density of 100 strips per inch (39.37 strips per cm). Also, the widths of strips 117 preferably equals the spacings between them. Part of the incoming light beam 114 is reflected as first layered or laminated beams 122 by the metal strips 117 on the patterned mirror 115; part is transmitted as second layered beams 125 (shown as dashed lines) through the glass 119 of the patterned mirror 115 to a first sizing lens 128.

The first sizing lens 128 can be of one meter (39.37 in.) focal length and it serves the function of decreasing the effective object-to-image path of the infrared light in beams 125. A sizing lens of Model No. 94746 and available from Edmund Scientific Co. can be used. The second layered light beams 125 are reflected by an infrared (IR)-reflecting dichroic mirror 131 (commonly called a hot mirror) to a second hot mirror 133 and thence as second projected layered beams 135. The two hot mirrors 131 and 133 function to filter out and substantially eliminate visible light from the second layered light beams, thus providing the second projected layered beams 135 as containing relatively pure infrared radiation. The visible light which is filtered out is indicated as beams 138.

The first layered light beams 122 are reflected by a visible-reflecting dichroic mirror 141 (commonly called a cold mirror) to the second hot mirror 133 and pass therethrough as first projected layered beams 144. Reflection by the cold mirror 141 and transmission by the hot mirror 133 function to filter out and substantially eliminate infrared radiation from the first layered light beams 122. The infrared radiation which is filtered out is indicated as beams 147. Thus, the patterned mirror 115, the hot mirrors 131 and 133, as well as the cold mirror 141, provide a means for extracting light beams of an infrared frequency band and of a visible frequency band from radiation of different wavelengths provided by a source 106.

The proper positioning of patterned mirror 115 and dichroic mirrors 131, 131 and 141, will place the irst projected layered beams 144 into registration with the second projected layered beams 135. The hot mirror 133 can be viewed as a registration target in this connection. The registered first and second projected beams 135 and 144 travel through a transmitting lens 151 and are focused thereby as an image 156 containing a pattern of alternating stripes on an object or part 159 to be inspected. The transmitting lens 151 preferably reduces the size of the image by a factor of 3 so that the spatial density of the stripes projected onto the part 159 is now 300 lines per inch (118.1 lines per cm) as opposed to 100 lines per inch (39.37 lines per cm) generated at the patterned mirror 115. Thus, an image 156 of an object, namely the patterned mirror 115, is projected onto the part 159. The image 156 can be viewed as comprising subimages contained in the layered beams 122 and 125.

The image 156 is reflected by the part 159 as beams 159A to a receiving lens 161 which is preferably positioned near the part 159 and preferably positioned along an axis which forms approximately a 27° angle, namely angle 163, with the registered projected beams 135 and 144. The receiving lens 161 projects the reflected image as a reflected light beam 166 (which still contains registered layers of light but perhaps altered by surface features of the part 159) to a second cold mirror 169. Cold mirror 169 reflects visible light as first reflected layered beams 175 and filters out and transmits IR radiation as second reflected layered beams 178. A visible-passing filter 181 may be present in the path of the first reflected beams 175 to further filter out IR radiation to provide first reflected layered beams 175A comprising substantially pure visible light. A first camera 183 which may comprise an array of photodiodes is positioned in the path of the first reflected layered beams 175A.

Figure 3:
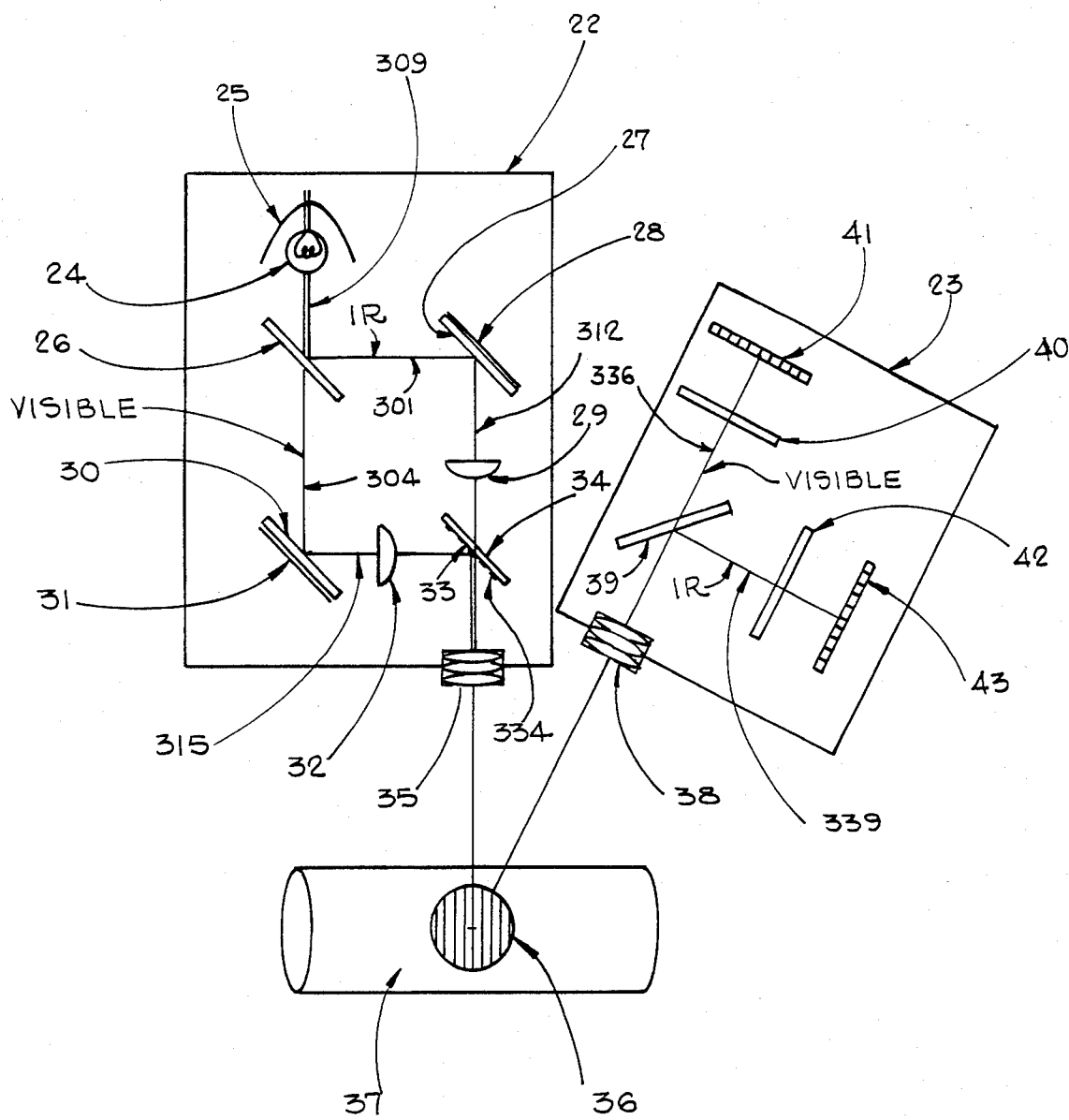
FIG. 3 represents an invention in the prior art.

The second reflected layered beams 178 may travel through an IR-passing filter 185 which further filters out visible light and provides second reflected layered light beams 178A comprising substantially pure infrared light. A second sizing lens 188, which can be identical to the first sizing lens 128, is placed in the path of the second reflected layered beams 178 to decrease the effective object-to-image distance traveled by these beams 178. These beams 178 are projected to a second camera 191 which can comprise an array of photodiodes which are sensitive to infrared radiation. The two cameras 183 and 191 provide collections of signals which are transmitted to signal processing circuitry (not shown). The signal processing circuitry generates signals indicative of the spatial sequence of the intensity of the reflected radiation. Greater detail concerning components described in FIG. 3 is contained in the allowed patent application of Joseph L. Mundy, et al., entitled "Non-Contact Measurement of Surface Profile," Ser. No. 158,372, filed June 11, 1980. That application is assigned to the same assignee as the present application and the application of Mundy, et al., is hereby incorporated by reference and further discussed below in the section entitled "General Considerations."

The receiving lens 161 preferably focuses the image reflected by the part 159 onto the cameras 183 and 191 at a magnification of approximately 5. Thus, since the image 156 on the object 159 had a density of 300 lines per inch, the spatial density of the lines received by cameras 183 and 191 is approximately 60 lines per inch (23.6 lines per cm). It is to be noted that the images transmitted by the first and second reflected layered beams 175 and 178 could be placed into correct focus onto respective cameras 183 and 191 by positioning these cameras so that the paths traveled by these beams 175 and 178 are of a correct length to focus the frequency of light involved. In this case, the magnifications of the images would be different because image magnification is, as discussed below, dependent upon the distance from the focusing lens to the point where the image is produced. Therefore, the image received by camera 191 (the IR image) would be larger than that produced at camera 183 since the IR image would travel a longer distance. Thus, a different spatial density of the lines in the image 156 reflected by the part 159 would be seen by cameras 183 and 191. This different spatial density would cause significantly increased complexity in the signal processing equipment required. Hence, the first and second sizing lenses are utilized to allow the effective optical paths traveled by the infrared and visible beams from the condensing lens 112 to their respective cameras 183 and 191 to be of identical length.

The patterned mirror 115 is positioned at an angle, namely angle 195, of generally 45°, with respect to light beam 114. As seen in FIG. 1, the length of the paths travelled by IR radiation from points 197 and 198 on patterned mirror 115 to points 199 and 200 on object 159 are respectively different. Thus, image portions at these points 199 and 200 will be in different focus, subject to the corrections to focus made by first sizing lens 128 and transmitting lens 151. To counter this effect, it is preferred that the object 159 be positioned as shown in FIG. 1A.

Figure 1A:
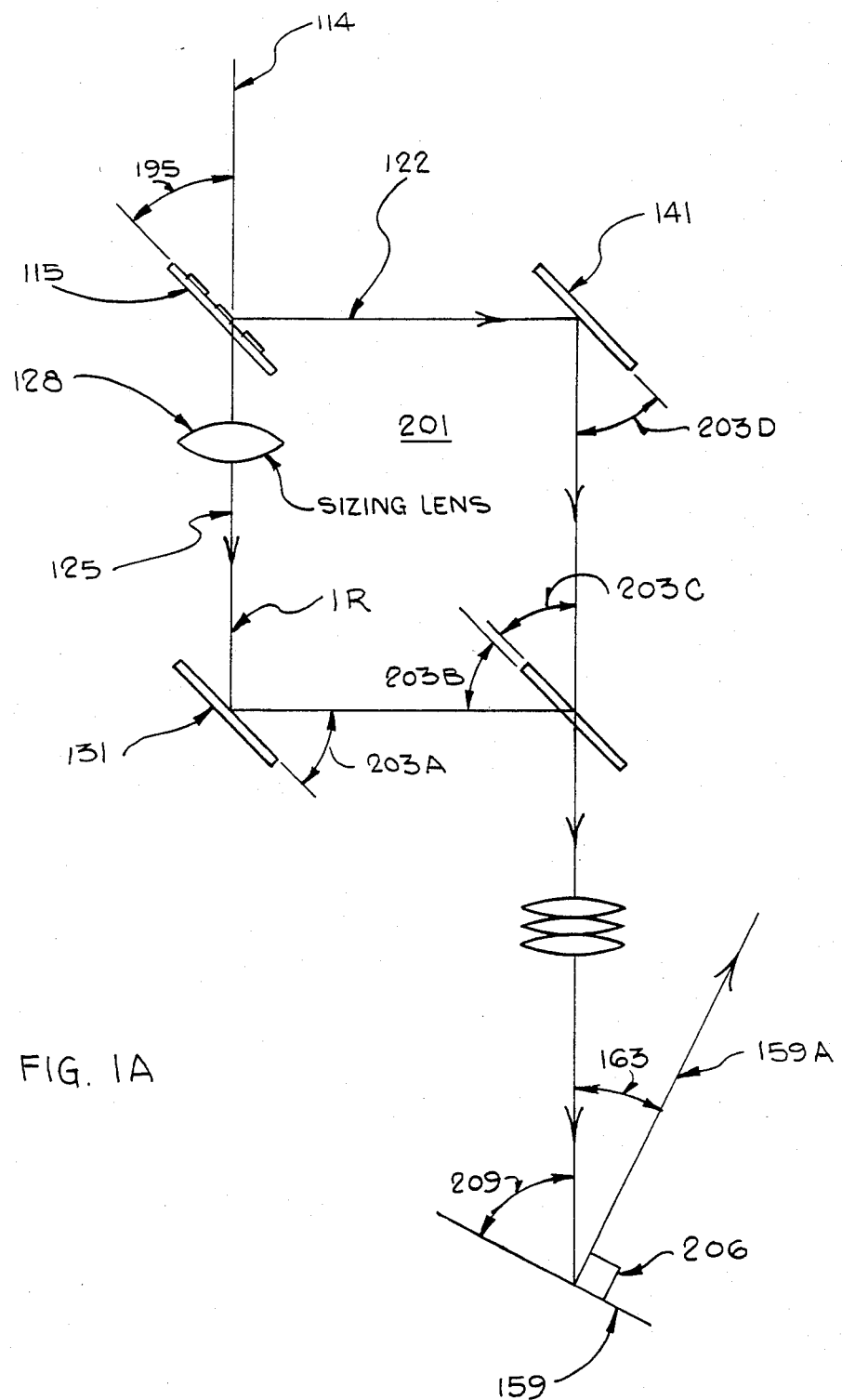
FIG. 1A is a simplified schematic view of part of the invention shown in FIG. 1.

In FIG. 1A, a side view is shown in which some of the light beams of FIG. 1 are shown, but as straight lines. Beams 122 and 125 are shown as forming two sides of a square 201. As mentioned, angle 195 is 45° and angle 163 is preferably 27°. Angle 206 is preferably 90°, thus requiring angle 209 to be 63°. Stated in other words, beam 159A is perpendicular to the surface of part 159: beam 159A is normal to the part. Except for the lack of parallelism due to angle 209, the surface of object 159 is preferably otherwise parallel with patterned mirror 115. (It is to be noted that arrays 183 and 191 in FIG. 1 are preferably substantially perpendicular to the light beams 175A and 178A.) As a result of the particular value of angle 163 in FIG. 1A, all portions of the image 156 in FIG. 1, such as the portions at points 199 and 200, will be in substantially the same degree of focus. The angle 163 required can be computed by ray tracing techniques, taking into account the magnification of the transmitting lens 151. (Of course, a magnification of unity would require angle 163 to be 45°, making the surface of object 159 parallel with patterned mirror 115 in all planes.)

An invention has been described which projects two beams of light, each containing alternating layers of different wavelengths and both in register to form an image on a part which image contains a striped pattern. Of course, other patterns, such as spirals, could be used. Both images are focused to substantially the same degree of precision and have substantially the same degree of magnification. The invention receives radiation reflected by the part, separates the registered beam into two beams of different temporal frequency and projects the two beams onto cameras with substantially the same degree of focus and substantially the same magnification. It is not seen as necessary that the two beams be projected simultaneously onto the part. The two beams could alternate in time.

GENERAL CONSIDERATIONS

One approach to the optical inspection of surfaces is to project a striped image comprising alternating stripes of two different frequencies of light onto the surface. Variations in the image as reflected from the surface are interpreted as indicative of variations in features at that surface. One such approach is illustrated in the patent application of Joseph L. Mundy, et al, mentioned above. FIG. 3 of the present application is a schematic representation of one form of the approach of Mundy, et al. (Numbers in FIG. 3 greater than 50 were not contained in that Figure as filed in the Mundy, et al, application, but were added by the present inventor for purposes of reference. The legends identifying the lenses were also added by the present invention). A light beam 301 containing primarily infrared (IR) radiation and a light beam 304 containing primarily visible light are extracted from a light beam 309 provided by a light source 24 by means of a dichroic mirror 26. An elliptical reflector 25 assists in gathering light from the source 24 and reduces the line-source characteristics of that source 24. A second dichroic mirror 27, having a light absorbing backing 28, extracts or filters out further visible light from beam 301 to provide a light beam 312 comprising substantially pure infrared radiation.

Another dichroic mirror 30, having a light absorbing backing 31, extracts or filters out IR radiation from the visible light beam 304 to provide a light beam 315 comprising substantially pure visible light. Light beams 312 and 315 are focused respectively by aspheric condensing lenses 29 and 32 onto a patterned mirror 33. The patterned mirror 33 has a bar pattern 34 on one surface comprising metalized strips 334 of equal widths, equally spaced from each other. Alternate portions of the infrared beam 312 are blocked by the metalized strips 334, and alternate portions of the visible light beam 315 are reflected by the metalized strips 334 toward an objective lens 35 which focuses the two beams, now traveling in register, into a complimentary color pattern image 36 on the surface of a part 37 to be examined.

The image 36 is reflected by the object 37 to an objective lens 38 which focuses the image to an IR reflecting dichroic mirror 39 which passes a visible light beam 336 through a visible pass filter 40 to a first linear photodiode array 41. The IR reflecting dichroic mirror 39 reflects an IR beam 339 through an IR pass filter 42 to a second linear photodiode array 43. The arrays 41 and 43 generate signals corresponding to information contained in the reflected image and these signals are transmitted to signal processing circuitry (not shown).

Figure 4:
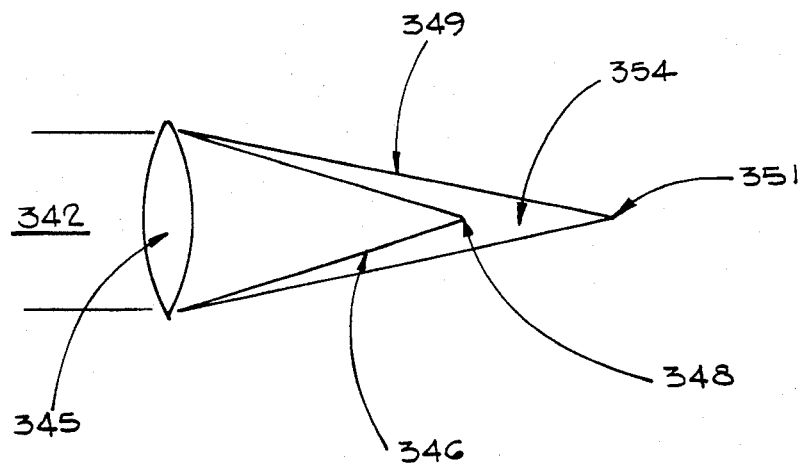
FIG. 4 illustrates light beams focused by a lens.

FIG. 4 is an illustration of the fact that light at different wavelengths is focused differently by the same lens. In general, the focal point of short wavelength light, such as blue light, will be nearer the focusing lens than the focal point of longer wavelength light such as red light. In FIG. 4, an incoming light beam 342 will be focused by lens 345 such that the focal point for the blue light 346 contained within the incoming beam 342 will be at a relatively near point 348, while the red light 349 contained within the incoming beam 342 will be focused at a relatively far point 351.

This is further illustrated by the lens maker's equation: $1/f=(n-1)\times k$, wherein f represents the focal length of a lens, n represents the index of refraction of the lens and k is a constant determined by the characteristics of the lens used. As an example, borosilicate crown glass exhibits an index of refraction of 1.49 for light of a wavelength of 10,000 angstroms (light in the mid-IR range) and an index of refraction of 1.52 for light of a wavelength of 5,000 angstroms (mid-visible range). Substituting these values of refractive indices for n in the lens maker's equation allows the conclusion that $f_{visible}/f_{IR}=49/52$. Viewed another way, the focal point for visible light is about 6% closer to the lens than the focal point for light in the mid-infrared range. Thus, since the paths followed by the visible and infrared beams in FIG. 3 in traveling from the light source 24 to the part 37 are the same length, both of the light beams cannot be in precise focus on the part. (Of course, if the part were located at a point between the visible focal point and the IR focal point, such as point 354 in FIG. 4, the two light beams 346 and 349 can have the same degree of misfocus.) Thus, the portion of the image 36 in FIG. 3 produced by the visible light beam 315 will possess a different degree of focus than the portion produced by IR light beam 312. This difference affects the degree of resolution which can be obtained by the signal processing circuitry concerning surface details of the part 37. With the resolution obtained by the present invention, surface details 0.0005 in. wide×0.005 in. long (0.00127 cm×0.0127 cm) have been detected.

While one embodiment of the present invention has been described, it will be obvious to a person skilled in the art that numerous modifications and substitutions can be undertaken without departing from the true spirit and scope of the present invention. Further, in scientific usage, the term "light" is sometimes restricted to visible electromagnetic radiation. However, for simplicity, this term in the claims is intended to cover all such radiation which can be focused by lenses, including infrared and ultraviolet radiation. Still further, the use of visible and infrared radiation has been discussed. However, the invention is not seen as limited to these two particular kinds of radiation. Also, the term "focus" refers to the degree of clarity of an image, i.e., the degree to which the image corresponds to the object (which may itself be an image) producing the image. "Magnification" refers to the size of the image as compared with the size of the object (or image) producing the image. The terms "band" and "frequency band" indicate that the light to which the terms refer is not of one discrete frequency, but comprises a range or band of frequencies. However, the terms "band" and "frequency band" are intended to cover light of one discrete frequency.

What is desired to be secured by Letters Patent is the invention as defined by the following claims.

I claim:

1. An optical projector comprising:
   (a) means for providing light beams of different wavelengths from light provided by at least one light source and
   (b) means for projecting the light beams of different wavelengths to an object at substantially the same degree of focus and at substantially the same magnification.

2. An optical projector comprising:
   (a) a source of light,
   (b) means for extracting first and second light beams of different frequencies from the light,
   (c) means for projecting the first and second light beams to form an image, and
   (d) means for focusing the first and second beams to substantially the same degree of focus in the image and to substantially the same magnification.

3. An optical projector according to claim 2 in which the means for focusing of 2 (a) comprises a sizing lens.

4. Optical projector comprising:
   (a) an illumination source for providing a light beam containing at least a first and a second frequency band;
   (b) reflective means for deriving a first and a second derivative light beam from the light beam, each of the beams comprising parallel layers of light;
   (c) first filter means for removing substantially all of the light of the second frequency band from the first derivative beam;
   (d) second filter means for removing substantially all of the light of the first frequency band from the second derivative beam; and
   (e) registration means for placing the first and second derivative beams into registration for projection to an object.

5. Projector according to claim 4 in which the first frequency band consists substantially of infrared frequencies and the second frequency band consists substantially of visible frequencies.

6. Projector according to claim 4 or 5 and further comprising a sizing lens located in the path of one of the beams.

7. Optical inspection system comprising:
  (a) pattern generation means for projecting a plurality of predetermined patterns of light, all patterns being substantially in focus and at substantially the same magnification, onto an object for reflection thereby; and
  (b) optical detector means for receiving some of the reflected light and for producing a collection of signals indicative of a reflected intensity distribution.

8. A system according to claim 7 in which the predetermined patterns of light comprises successively spaced parallel stripes of light.

9. A system according to claim 8 in which the successively spaced parallel stripes comprise stripes of two alternating frequency bands.

10. An inspection system comprising:
  (a) means for projecting to an object for reflection thereby a laminated beam of light having layers of a predetermined spatial sequence of frequencies; and
  (b) means for generating a plurality of signals in response to the reflected light indicative of a spatial sequence of the intensity of one of the reflected radiation frequencies.

11. Optical projector for projecting light to an object for reflection thereby comprising:
  (a) an illumination source providing a light beam containing visible and infrared light;
  (b) reflective grating means positioned near the illumination source for defining parallel layers of light of equal thickness in the light beam and for reflecting alternate layers out of the path of the remaining layers;
  (c) first filter means for substantially separating the visible light from the infrared light in the reflected alternate layers;
  (d) first reflection means for reflecting the visible light in the layers filtered by the first filter means to a registration target for transmission therethrough;
  (e) second filter means for substantially separating the visible from the infrared light in the remaining layers; and
  (f) second reflection means for reflecting the infrared light in the layers filtered by the second filter means to the registration target for reflection thereby and for coacting with the first reflection means to place the light layers reflected by each into registration at the registration target.

12. Projector according to claim 11 in which the first filter means and the first reflection means are the same unit and in which the second filter means and the second reflection means are the same unit.

13. Projector according to claim 11 in which the registration target comprises a dichroic mirror.

14. Projector according to claim 11 and further comprising a sizing lens positioned in the path of the remaining light layers of 11 (e).

15. Projector according to claim 11 and further comprising a lens means for focusing the registered light beam to an examination target.

16. Projector according to claim 11 and further comprising:
  (a) receiving lens means for receiving light reflected by the object,
  (b) filter means receiving light from the receiving lens and for substantially separating the infrared from the visible light therein,
  (c) a first camera means for receiving the visible light and for generating signals in response thereto,
  (d) a second camera means for receiving the infrared light and for generating signals in response thereto, and
  (e) a sizing lens for producing similarity in magnification in the light received by the first and second camera means.

17. Projector according to claim 11 in which both cameras comprise photodiode arrays positioned substantially perpendicularly to the respective light beams each receives.

18. Projector according to claim 1, 2, 4, 11 or 16 in which the light projected to the object strikes the object at substantially 27° off perpendicular and at a demagnification of 3 when compared with the light provided by the source.

19. In a surface inspection system of the type including a light source, first separation means for separating light provided by the light source into light beams of two different frequencies, means for placing the beams in registration for projection of an image to an object for reflection thereby, second separation means for separating the reflected light into two beams of different frequencies, and camera means for producing signals in response to the two separated reflected light beams, the improvement comprising:
  (a) means for generating two subimages in the light received from the light source prior to separating the light into two beams of two different frequencies and for directing the two subimages in paths following two different directions,
  (b) a sizing lens placed in the path of one of the subimages of (a), and
  (c) a sizing lens placed in the path of one of the two separated reflected light beams.

20. The apparatus according to claim 19 in which the light source contains a filament and the filament produces an image from which the subimages of (a) are derived.

21. A method of optically inspecting an object, comprising the steps of:
  (a) a projecting light to a reflective grating for reflecting layers of light in one direction and for transmitting alternate layers of light in another direction,
  (b) extracting light of one frequency band from the reflected layers of light,
  (c) extracting light of a second frequency band from the transmitted alternate layers of light,
  (d) projecting the transmitted alternate layers of (c) through a sizing lens,
  (e) placing the layers of (b) and (c) into registration to form registered layers,
  (f) projecting the registered layers to an object for reflection,
  (g) separating some of the light reflected by the object into two beams of different frequencies,
  (h) projecting one of the two beams of (g) through a sizing lens, and
  (i) focusing at least one of the beams of (g) onto a camera for producing signals in response.

22. An optical projector comprising:

(a) means for generating first and second projected images of different frequencies traveling along first and second optical paths;

(b) sizing means interposed in one of the optical paths of (a) for adjusting the focus and magnification of the first projected image independently of the second projected image;

(c) means for combining the first projected image as adjusted in (b) with the second projected image and projecting the combined image to a part (159);

(d) means for extracting two reflected images from the combined image of (c) and for projecting the extracted images along separate paths to separate sensors; and (e) second sizing means interposed in one of the paths of (d) for adjusting the focus and magnification of one of the reflected images independently of the other reflected image.

* * * * *